United States Patent [19]
Schwall et al.

[11] 3,944,483
[45] Mar. 16, 1976

[54] DISTILLATIVE RECOVERY OF AROMATICS WITH WATER ADDITION IN AZEOTROPIC PROPORTIONS

[75] Inventors: Fritz Schwall; Gerhard Preusser, both of Essen; Martin Schulze, Neviges, all of Germany

[73] Assignee: Krupp-Koppers GmbH, Essen, Germany

[22] Filed: Dec. 20, 1973

[21] Appl. No.: 426,790

[30] Foreign Application Priority Data
Dec. 20, 1972   Germany............................ 2262303

[52] U.S. Cl. .................... 208/321; 203/26; 203/46; 203/92; 260/674 SE
[51] Int. Cl.² ......................................... C10G 21/28
[58] Field of Search ....... 203/96, 95, 97, 58, 43–46; 260/674 SE, 674 R; 208/326, 321, 324; 196/139, 140

[56] References Cited
UNITED STATES PATENTS

| | | | |
|---|---|---|---|
| 2,648,624 | 8/1953 | Hess et al. ............................. | 203/58 |
| 2,730,558 | 1/1956 | Gerhold .............................. | 208/321 |
| 2,737,538 | 3/1956 | Nelson ................................ | 203/58 |
| 2,886,610 | 5/1959 | Georgian ............................ | 208/321 |
| 2,981,661 | 4/1961 | Black .................................... | 203/96 |
| 3,071,632 | 1/1963 | Schmid ................................ | 203/46 |
| 3,114,783 | 12/1963 | Butler et al. .......................... | 203/58 |
| 3,132,078 | 5/1964 | Backlund .............................. | 203/58 |
| 3,207,692 | 9/1965 | Van Kleef et al. ................... | 208/321 |
| 3,655,806 | 4/1972 | Brandt et al. ......................... | 203/43 |
| 3,702,295 | 11/1972 | Thompson .......................... | 208/321 |
| 3,714,033 | 1/1973 | Somekh et al. ..................... | 208/321 |
| 3,714,034 | 1/1973 | Kosseim et al. ..................... | 208/321 |

*Primary Examiner*—Norman Yudkoff
*Assistant Examiner*—Frank Sever
*Attorney, Agent, or Firm*—Michael J. Striker

[57] ABSTRACT

A hydrocarbon mixture consisting of an aromatic and a non-aromatic component is subjected to a liquid-liquid extraction and/or an extractive distillation. A solvent is used which selectively dissolves the aromatic component so as to form an extract phase. The extract phase is introduced into a distillation column for separating the solvent and the aromatic component. The column is provided with trays and the extract phase is introduced into the column at about the middle thereof from where the solvent flows downwardly and the aromatic component flows upwardly. Sufficient water is introduced into the sump of the column to insure that the trays above the location at which the extract phase enters the column are filled with water during the separation. This improves the operation of the distillation column. An arrangement for carrying out the above process is also disclosed.

14 Claims, 1 Drawing Figure

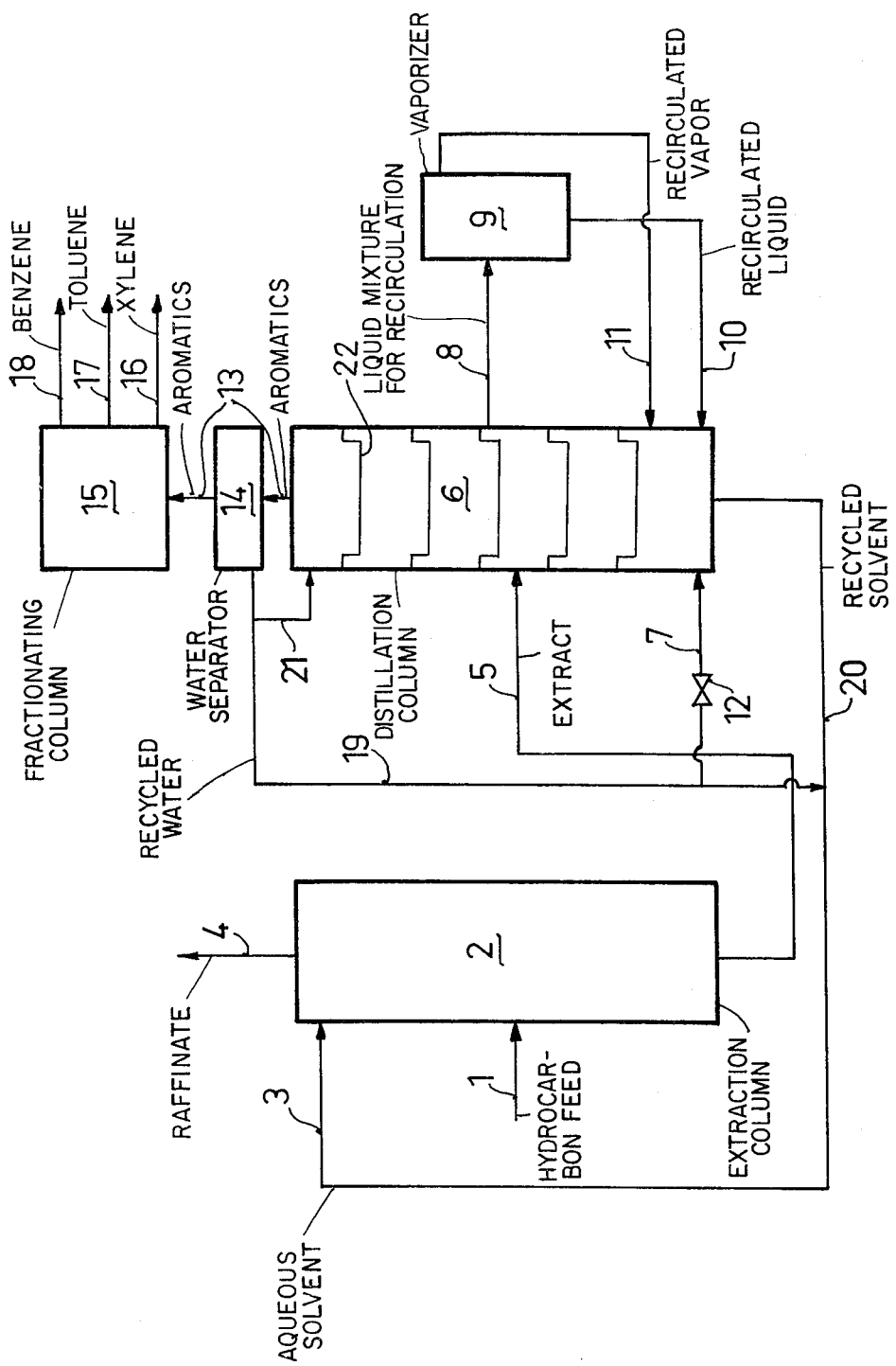

DISTILLATIVE RECOVERY OF AROMATICS WITH WATER ADDITION IN AZEOTROPIC PROPORTIONS

BACKGROUND OF THE INVENTION

The invention relates generally to the recovery of individual components from mixtures of different components and, more particularly, to the recovery of high-purity aromatic substances from hydrocarbon mixtures containing both aromatic and non-aromatic components.

A process for the recovery of high-purity aromatic substances from hydrocarbon mixtures containing aromatic and non-aromatic components in any relative proportions is already known. The hydrocarbon mixture is subjected to a liquid-liquid extraction and/or an extractive distillation using an aqueous solvent which is selective towards one of these components. The bottom product or extract phase formed in the extraction apparatus, which consists mainly of the aromatic component and the solvent, is withdrawn and then introduced into a separating column or distillation column wherein the extract phase is separated into an aromatic fraction and a solvent fraction. The top product or raffinate phase formed in the extraction apparatus, which consists mainly of the nonaromatic component, is also withdrawn from the extraction apparatus.

The known process outlined above is, in practice, used with many variations and with a large number of different types of aqueous, selective solvents. The addition of water to the solvent serves, among other things, to improve the selectivity of the solvent. As an example, a combined process is known from the German published application No. 2,040,025 wherein a liquid-liquid extraction is followed by an extractive distillation. The selective solvent used here is a mixture of morpholine and/or N-substituted morpholines with water. The water content of the solvent for the liquid-liquid extraction lies between 2 and 15% by weight whereas the water content of the solvent for the extractive distillation is up to 8% by weight.

When using aqueous solvents, however, particular problems arise in the operation of the separating column wherein the solvent and the aromatic component are separated which do not arise when non-aqueous solvents are used and where, consequently, it is only necessary to drive off the solvent, i.e. where no water must be driven off. In this connection, it must be taken into account that the aromatic component of the extract phase has to be separated as completely as possible, for example, so that at most about 0.1% by weight is left behind, in order to impart good efficiency to the process. Although it is true that the water content of the aqueous solvents provides for a lower bottom temperature in the separating column as compared to the case where non-aqueous solvents are used, it has, on the other hand, been frequently observed that the operation of the separating column becomes irregular or fluctuates when using aqueous solvents. The trays of the column become partially flooded or inundated and it is not possible to maintain either the bottom temperature or the column temperature constant.

A further problem which arises in the separating column when aqueous solvents are used is due to the fact that the possibility of hydrolysis of the solvent exists. Of course, very significant differences exist between the various solvents in this regard. However, because of the severe temperature requirements imposed upon the solvents during the operation of the separating column, even very stable solvents will undergo a certain amount of hydrolysis, albeit small. Thus, during the operation of the separating column, it is necessary to insure to as great an extent as possible that the degree of hydrolysis of the solvent is held to a minimum and that the products of the hydrolysis do not contaminate the aromatic fraction withdrawn at the top of the separating column.

It will, therefore, be seen that improvements in the recovery of high-purity aromatic substances from hydrocarbon mixtures are desirable.

SUMMARY OF THE INVENTION

It is, accordingly, a general object of the present invention to provide a novel process and arrangement for the recovery of individual components from mixtures of different components.

More particularly, it is an object of the invention to provide a process and arrangement for the recovery of aromatic substances from hydrocarbon mixtures whereby the operating conditions of the separating column are so improved that it operates smoothly and without fluctuations and that no temperature variations occur.

A further object of the invention is to provide a process and arrangement for the recovery of aromatic substances from hydrocarbon mixtures whereby hydrolysis of the solvent is held to a minimum and whereby the products of the hydrolysis do not contaminate the aromatic substance withdrawn from the separating column.

An additional object of the invention is to provide a process and arrangement for the recovery of aromatic substances from hydrocarbon mixtures whereby the separating effect of the separating column is improved.

In pursuance of these objects, and of others which will become apparent, the invention provides, in a process for the recovery of high-purity aromatic substances from hydrocarbons, for treating a hydrocarbon mixture including an aromatic and a non-aromatic component with a solvent so as to form an extract phase container at least part of the solvent and at least a portion of one of the components. The extract phase is admitted into a separating column having two ends and wherein the aforesaid one component flows towards one of these ends and the solvent flows towards the other end. The extract phase is admitted into the column at a location intermediate the ends thereof and the section of the column between this location and the end thereof towards which the aforesaid one component flows is provided with trays. A quantity of water sufficient to maintain at least some of these trays substantially filled with water during separation of the solvent and the aforesaid one component is introduced into the column.

The hydrocarbon mixture may contain the aromatic and non-aromatic components in any proportions. This mixture may be treated with a liquid-liquid extraction and/or an extractive distillation using an aqueous, selective solvent. The extract phase resulting from this extraction procedure is the bottom product of the extraction apparatus and may contain a substantial portion, if not all, of the aromatic component of the hydrocarbon mixture. This extract phase is then admitted into a separating or distillation column. The top product of the extraction apparatus, that is, the raffinate phase, may contain most, if not all, of the non-aromatic component of the hydrocarbon mixture. This raffinate phase is also withdrawn from the extraction apparatus and may subsequently undergo further treatment.

In accordance with the invention, at least some of the trays of the separating column above the inlet for the extract phase are maintained filled with water during the period in which separation of the solvent and the aromatic component of the extract phase occurs. Moreover, the invention further provides for operating the separating column with water reflux.

The additional water introduced into the separating column according to the invention may be introduced into the sump of the separating column. The thus-introduced water distills or vaporizes, rises in the column and then condenses on the trays. The required quantity of water in the sump of the separating column may be very simply obtained by admitting the necessary quantities of water into the sump from any convenient source. The water introduced into the separating column may be either in liquid or vapor phase. Normally, the amount of water which must be introduced into the separating column will be about 60–100% by weight of that required to form an azeotrope with the aromatic component of the extract phase.

Usually, the separating column is provided with trays along its entire length. In accordance with a favorable modification of the invention, an outlet is provided at one of the trays in the middle region of the column through which the liquid mixture on the tray is withdrawn and returned to the sump. In this instance, the requisite quantity of water in the sump may be adjusted by the mixture thus returned into the separating column. This modification of the invention may be further varied by providing a vaporizer through which the liquid mixture withdrawn from the tray is passed before being returned to the sump. Here, a partial vaporization of the withdrawn mixture occurs and the vapor and liquid are introduced into the sump of the separating column at spaced locations. The inlet for the vapor should be located above that for the liquid.

Although, on the grounds of thermal efficiency, it has always been attempted heretofore to hold the amount of water admitted into the separating column to a minimum, it has now been surprisingly found that, by increasing the quantity of water in the separating column, an improvement in the separation effect may be achieved. Thus, first of all, if the quantity of water is regulated to the value set forth by the invention by introducing additional water into the sump of the separating column, the temperature for effecting separation is lowered. For example, whereas the separating temperature for a product containing benzene, toluene and xylol is about 244°C at atmospheric pressure when the separating column is operated free of water, the separating temperature is lowered to 160°C when using water. Furthermore, because the trays above the inlet for the extract phase are filled with water according to the invention, the upper portion of the separating column serves as a sort of separation layer. In other words, the aromatic substances do not flow back through the upper portion of the separating column which, as a result, serves as a separation layer. Thus, the aromatic substances flow upwardly through the separating column to be withdrawn at the top thereof and, since the trays in the upper portion of the column are filled with water, it is not possible for the aromatic substances to penetrate through the trays and flow downwardly.

Since it is not possible for the aromatic substances to reflux to the trays below the inlet for the extract phase and into the bottom portion of the separating column where the solvent is located, it is also not necessary to again separate them from the solvent. However, as extensive research has shown, the irregular and fluctuating operation of the separating columns heretofore was due to an uncontrollable filling of the trays with water and aromatic substances to be driven off because these substances are not miscible and their different densities led to an uncontrollable filling of the trays of the separating column and an irregular discharge from the separating column. This is now avoided in accordance with the invention.

The volume of water to be introduced into the sump of the separating column is, according to the invention, of course dependent upon the type and quantity of the aromatic substances to be driven off or separated. Normally, the quantity of water will equal about 60–100% by weight of that required to form an azeotrope with the aromatic substances to be distilled or separated. As example:

100 parts by weight of benzene = 9.4 parts by weight of water
100 parts by weight of toluene = 15.6 parts by weight of water
100 parts by weight of xylol = 66.7 parts by weight of water The above quantities of water are those required to effect a good, trouble free separation or distillation of the aromatic substances. It will be appreciated that a person of ordinary skill in this art may easily determine the quantity of additional water required.

The relatively great decrease in the separating temperature which results from the addition of water in accordance with the invention has the further advantage that, because of the lower temperature requirements, the danger of possible decomposition or degradation of the solvent is decreased. In this regard, it is to be kept in mind that any organic solvent which is subjected to severe temmperature requirements will, in the course of time, undergo some changes. The types of changes and the extents of these changes will, however, vary from solvent to solvent. For the case presently under discussion, the change undergone by the solvent will mostly be a hydrolysis reaction. In any event, it must always be attempted to avoid contamination of the separated aromatic substances by the decomposition or hydrolysis products of the solvent.

This objective is achieved by a second condition in accordance with the invention whereby the separating column is operated with water reflux rather than with reflux of the aromatic substances as conventionaliy done heretofore. By this means, it is assured that the trays above the inlet for the extract phase remain filled with water under all circumstances without, however, requiring that water in excess of the azeotropic value be introduced into the sump of the separating column. Also, the upper trays of the separating column with their water filling serve as a water wash or scrub for the upwardly flowing aromatic substances. The vapors of the aromatic substances are then distilled out of the separating column in form of an azeotropic mixture with water. As an example, a comparison is given below of the boiling points of some aromatic substances when they are in pure form and when they are in azeotropic mixture with water to illustrate the decrease in boiling temperature obtained when aromatic substances are distilled in form of an azeotropic mixture with water:

|  | Boiling Point (pure) | Boiling Point (in azeotropic mixture with water) |
| --- | --- | --- |
| benzene | 80°C | 69°C |
| toluene | 110°C | 84°C |
| O-xylol | 144°C | 94°C |

The decrease in boiling temperature is always desired because, as a result, the difference in the boiling temperatures of the aromatic substances and the decomposition or hydrolysis products of the solvent is usually increased and, in many cases, it would be virtually impossible to separate the aromatic substances and the decomposition or hydrolysis products of the solvent from one another by distilling means without this decrease in boiling temperature. The decrease in boiling temperature thus works in addition to the washing effect which occurs in the uppermost, water-filled trays of the separating column and which is based on the different water solubilities of the aromatic substances and the decomposition or hydrolysis products of the solvent.

An extensive investigation by the instant applicants of the composition of the liquid mixture on the individual trays of the separating column has shown that a concentration of the decomposition or hydrolysis products of the solvent occurs on those trays which are located at or near the center of the separating column. Since essentially only water is present on these trays in addition to the decomposition or hydrolysis products, this recognition makes possible the use of a particular modification of the invention. According to this modification, and as already mentioned earlier, an outlet is branched off from one of the trays in the middle or center region of the column through which a portion of the liquid mixture forming on this tray is returned to the sump of the separating column. By the use of this embodiment, it is possible, on the one hand, to adjust the quantity of water in the sump to the desired value without requiring a continuous introduction of water from externally of the separating column. On the other hand, the possibility of the decomposition or hydrolysis products of the solvent concentrating in the upper portion of the separating column is thereby reduced. On the contrary, these products remain predominantly in the sump of the separating column after being returned thereto.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

The single FIGURE is a diagrammatic illustration of an arrangement for carrying out the process according to the invention.

DESCRIPTION OF THE PREFERRED EMBODIMENTS

Referring now to the drawing, a hydrocarbon mixture which is to be subjected to separation or extraction is introduced into an extraction apparatus for treating means 2 via a conduit 1. The hydrocarbon mixture contains both an aromatic and a non-aromatic component. It is not necessary here to go into the details of the extraction process or into the structural details of the extraction apparatus 2 since these are well known in the art. It is sufficient to state here that the hydrocarbon mixture may be subjected to a liquid-liquid extraction and/or an extractive distillation and, although the extraction apparatus 2 is here shown as consisting of a single column for the sake of clarity, it will be understood that the extraction apparatus 2 may include more than one column such as, for example, if the hydrocarbon mixture were first subjected to a liquid-liquid extraction and subsequently subjected to an extractive distillation. In fact, the construction of the extraction apparatus 2 may be arbitrarily chosen to suit particular requirements.

An aqueous, selective solvent is introduced into the extraction apparatus 2 via a conduit 3. The treatment of the hydrocarbon mixture in the extraction apparatus 2 results in the formation of a raffinate phase containing the non-aromatic component or substances of the mixture and this raffinate phase is withdrawn from the extraction apparatus 2 as a top product through the outlet conduit 4. The thus-withdrawn raffinate phase may be subjected to further treatment the details of which are, however, of no concern here.

The treatment of the hydrocarbon mixture in the extraction apparatus 2 further results in the formation of an extract phase which includes at least part of the aqueous solvent and a portion, perhaps most if not all, of the aromatic component or substances of the mixture. The extract phase comprising the aromatic component and the aqueous solvent is withdrawn from the sump or bottom of the extraction apparatus 2 and is from there admitted into the separating or distillation column 6 via the inlet conduit 5. The column 6, which is seen to be vertically oriented, is provided with trays or plates 22. The product admitted into the column 6, which is a mixture of aromatic substances, solvent and water, is normally introduced therein in the region of the middle or center of the column 6 as shown.

According to the invention, an inlet conduit 7 is provided which opens into the sump or bottom end of the column 6 and through which water, in either liquid or vapor form, may be introduced into the column 6. The inlet conduit 7 is provided with a valve 12. An outlet conduit 8 is also provided and communicates with one of the trays 22 in the middle or center region of the column 6, for example, the 15th tray. The outlet conduit 8 permits the withdrawal of the liquid mixture which accumulates on this tray. In the illustrated embodiment, the outlet conduit 8 communicates with a vaporizing apparatus 9 in which the liquid mixture withdrawn through the outlet conduit 8 may undergo a partial vaporization. After the partial vaporization, the vapor and liquid are removed from the vaporizer 9 through separate conduits 10 and 11 which lead into and communicate with the sump of the column 6. It will be seen that the conduit 11, through which the vapor is returned into the column 6, is located above the conduit 10 through which the liquid is returned into the column 6.

At the start of the operation of the column 6 it is necessary to introduce water therein via the inlet conduit 7 so that there is sufficient water in the sump of the column 6 to insure that the trays above the location where the extract phase is introduced into the column 6 by the conduit 5 are filled with water. The additional water thus introduced into the sump of the column 6 vaporizes or evaporates, rises upwardly through the column 6 and condenses on these trays. However, when the arrangement illustrated is provided with the conduits 8, 10 and 11, it may be possible under certain circumstances to maintain the requisite quantity of water, that is, the quantity of water necessary to assure that the trays above the location at which the conduit 5 communicates with the column 6 are filled with water, in the sump of the column 6 by admitting the mixture withdrawn from the column 6 by the conduit 8 into the sump via the conduits 10 and 11. In this case, the valve 12 may remain closed during operation of the column 6 so that no water is introduced into the latter via the inlet conduit 7.

It is, of course, also possible to eliminate the vaporizer 9 or, in other words, to have the conduit 8 communicate directly with the sump of the column 6 so that no partial vaporization of the liquid mixture withdrawn from the column 6 via the conduit 8 occurs. Where the vaporizer 9 is provided, this may be arranged in heat-exchange relationship with other parts of the arrangement used for carrying out the process, that is, with one or more parts of the arrangement used for the recovery of high-purity aromatic substances from the hydrocarbon mixture.

The aromatic substances from the extract phase flow upwardly in the column 6 towards the upper end or top thereof. The aromatic substances are withdrawn from the column 6 at its upper end and pass into a water separator 14 via a conduit 13 where residual water is separated from the aromatic substances. The aromatic substances next pass through the conduit 13 into a column 15 where they are further split up into their individual components such as, for example, a benzene, a toluene and a xylol fraction. The latter products may be conveyed from the column 15 via the conduits 16, 17 and 18.

The water collected in the water separator 14 may be removed therefrom via the conduit 19. It will be seen that another conduit 21 branches off from the conduit 19. The conduit 21 communicates with the upper end of the column 6 and it is through the conduit 21 that the requisite quantity of water flows which is refluxed to the top of the column 6. This refluxed water insures that the trays in the upper portion of the column 6, that is, the trays above the location at which the conduit 5 communicates with the column 6, are filled with water under all circumstances and without requiring that a quantity of water in excess of that necessary to form an azeotropic mixture with the aromatic substances in the extract phase be introduced into the sump or lower end of the column 6. That portion of the water withdrawn from the water separator 14 and which flows through the conduit 19 but is in excess of that which must be refluxed into the top of the column 6 continues flowing through the conduit 19 towards the inlet conduit 7. By appropriate adjustment of the valve 12, this excess water may flow back into the sump of the column 6 via the inlet conduit 7. If the valve 12 is only partially opened or if the valve 12 is closed, then the excess water which does not flow through the inlet conduit 7 continues on through the conduit 19 and flows into the conduit 20. The conduit 20 communicates with the sump of the column 6. The solvent contained in the extract phase entering the column 6 via the conduit 5 flows downwardly in the column 6 to the sump thereof to concentrate there and is withdrawn from the sump via the conduit 20. Thus, the excess water in the conduit 19 which flows into the conduit 20 is recycled back into the solvent circuit and serves in adjusting the water content of the aqueous solvent. The solvent passes from the conduit 20 into the conduit 3 and, from the latter, is again admitted into the extraction apparatus 2.

Although, for the sake of clarity, only the valve 12 has been shown in the drawing, it will be understood that appropriate valves or other regulating means will be provided where necessary or desired. It will also be appreciated from the foregoing description that the conduits 7, 8 and 21, the water separator 14 and, where present, the conduits 10 and 11 and the vaporizer 9, all constitute part of a means for introducing water into the column 6 and for maintaining the trays in the upper section thereof, that is, the trays above the location at which the conduit 5 communicates with the column 6, filled with water. Of course, such a means may include other elements which, however, have been omitted for ease of understanding of the invention.

The effect of the invention may be seen from the following comparative investigation. In either case, the aromatic-containing extract had been previously subjected to a liquid-liquid extraction using a selective solvent with a water content of 4.5% by weight. In case A, the separating column was operated without the introduction of additional water so that the decrease in the boiling or distillation temperature was due solely to the water content of the solvent. In case B, the process according to the invention was used and the requisite quantity of water in the sump of the separating column was obtained by withdrawing part of the liquid mixture from the 15th tray of the column and returning this to the sump. Here, 2 cubic meters of liquid mixture containing about 1.9 tons of water was returned to the sump per unit of time. The following results were obtained:

|  | Case A | Case B |
| --- | --- | --- |
| Distillation Temperature (separating column 6) | 200°C | 160°C |
| Concentration in Solvent Withdrawn from Sump (conduit 20) | | |
| Benzene | 0.034% | 0.009% |
| Toluene | 0.211% | 0.034% |
| Xylol | 0.780% | 0.130% |
| Concentration of Solvent and its Decomposition Products in the Aromatic Phase Withdrawn from the Separating Column 6 (conduit 13) | 400 ppm | <1 ppm | s
It is emphasized here that the invention is not restricted to or limited by the use of a particular solvent.

It will be understood that each of the elements described above, or two or more together, may also find a useful application in other types of processes and arrangements differing from the types described above.

While the invention has been illustrated and described as embodied in a treatment for hydrocarbons, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended:

1. In a process for the recovery of aromatic hydrocarbons from mixtures which contain aromatic and non-aromatic hydrocarbons, comprising subjecting a mixture which includes an aromatic and a non-aromatic hydrocarbon to extractive treatment with a water-containing solvent so as to form an extract phase which contains at least part of said solvent and at least a portion of said aromatic hydrocarbon; admitting at least a portion of said extract phase into a distillation zone having an upper and a lower end portion; distilling said extract phase in said zone for recovery of said portion of said aromatic hydrocarbon; and introducing into said lower end portion of said zone a quantity of water, the improvement consisting essentially of, providing said quantity of water in an amount which equals between about 60 and 100 percent by weight of the amount of water required to form an azeotrope with said portion of said aromatic hydrocarbon, said quantity of water being additional to the water contained in said extract phase.

2. A process as defined in claim 1, wherein said extractive treatment comprises liquid-liquid extraction.

3. A process as defined in claim 1, wherein said extractive treatment comprises extractive distillation.

4. A process as defined in claim 1, wherein said extractive treatment comprises liquid-liquid extraction and extractive distillation.

5. A process as defined in claim 1, wherein said solvent selectively dissolves said aromatic hydrocarbon.

6. A process as defined in claim 1; further comprising the steps of withdrawing said aromatic hydrocarbon from said zone; separating residual water from the withdrawn aromatic hydrocarbon; and recycling the separated water.

7. A process as defined in claim 1, said zone including an upper section which is provided with a plurality of trays, and said extract phase being admitted into said zone at a location below said section; and wherein said quantity of water is sufficient to maintain at least some of said trays substantially filled during distillation.

8. A process as defined in claim 7, said zone including another section below said location which is also provided with trays; and wherein the step of introducing said quantity of water into said zone comprises withdrawing water from one of said trays and readmitting at least a portion of the withdrawn water into said zone.

9. A process as defined in claim 8, wherein said one tray is located in the middle section of said zone.

10. A process as defined in claim 8; and further comprising the step of partially vaporizing said withdrawn water prior to readmitting said withdrawn water into said zone.

11. A process as defined in claim 10, wherein the unvaporized part of said withdrawn water is introduced into said zone at a higher location than the vaporized part of said withdrawn water.

12. A process as defined in claim 10, wherein the step of partially vaporizing said withdrawn water comprises a heat-exchange between said withdrawn water and another fluid present in said process.

13. A process as defined in claim 1, wherein at least part of the water in said zone is refluxed.

14. A process as defined in claim 13, wherein at least part of the refluxed water is introduced into said zone at said upper end portion.

* * * * *